US008442639B2

(12) United States Patent
Walker et al.

(10) Patent No.: US 8,442,639 B2
(45) Date of Patent: May 14, 2013

(54) SYSTEMS AND METHODS FOR ELECTRICAL STIMULATION OF BLOOD VESSELS

(75) Inventors: Joseph Walker, Shoreview, MN (US); Rodney W. Salo, Fridley, MN (US); Anand Iyer, Lino Lakes, MN (US); Joseph M. Pastore, Woodbury, MN (US); Eric Mokelke, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 295 days.

(21) Appl. No.: 11/674,463

(22) Filed: Feb. 13, 2007

(65) Prior Publication Data

US 2008/0195174 A1 Aug. 14, 2008

(51) Int. Cl.
*A61N 1/00* (2006.01)
*A61B 5/04* (2006.01)

(52) U.S. Cl.
USPC .................. 607/44; 607/2; 607/116; 600/381

(58) Field of Classification Search .................... 607/44, 607/2, 116; 600/381
See application file for complete search history.

(56) References Cited

U.S. PATENT DOCUMENTS

| 5,725,563 | A * | 3/1998 | Klotz ............................ 607/62 |
| 6,450,942 | B1 | 9/2002 | Lapanashvili et al. |
| 6,522,926 | B1 | 2/2003 | Kieval et al. |
| 6,571,127 | B1 | 5/2003 | Ben-Haim et al. |
| 6,845,267 | B2 | 1/2005 | Harrison et al. |
| 2003/0055465 | A1 * | 3/2003 | Ben-Haim et al. ............. 607/40 |
| 2004/0010303 | A1 | 1/2004 | Bolea |
| 2004/0102818 | A1 | 5/2004 | Hakky et al. |
| 2004/0106954 | A1 | 6/2004 | Whitehurst et al. |
| 2006/0253161 | A1 | 11/2006 | Libbus et al. |
| 2010/0016212 | A1 | 1/2010 | Rubin et al. |

FOREIGN PATENT DOCUMENTS

| JP | 2004-500906 A | | 1/2004 |
| JP | 2001-513338 A | | 12/2005 |
| WO | WO 84/03219 | * | 2/1984 |
| WO | WO-99-03533 A | | 1/1999 |
| WO | WO-03/076008 A1 | | 9/2003 |
| WO | WO 2007/013065 | * | 2/2007 |
| WO | WO-2007/013065 A2 | | 2/2007 |

OTHER PUBLICATIONS

Machine translation of WO 1984/03219 from google.*

(Continued)

*Primary Examiner* — Nicole F Lavert
(74) *Attorney, Agent, or Firm* — Schwegman Lundberg & Woessner, P.A.

(57) ABSTRACT

Disclosed herein, among other things, is a system for electrical stimulation of blood vessels. An embodiment of the system includes at least one electrode having electrical contact with a blood vessel. The embodiment also includes a stimulation circuit electrically connected to the electrode, the circuit adapted to provide stimulation to the vessel. The embodiment further includes a controller connected to the circuit, the controller adapted to select frequency and voltage parameters for the stimulation circuit to selectively affect vascular therapy, including constriction of the vessel and dilation of the vessel. According to various embodiments, the stimulation circuit and controller are contained within an implantable medical device (IMD). The system also includes a sensor connected to the controller, and the controller initiates and adjusts therapy based on a signal received from the sensor, in varying embodiments.

26 Claims, 11 Drawing Sheets

OTHER PUBLICATIONS

Jordan, H. "Vascular Massage: Its Technique and Use" J Bone Joint Surg Am. 1935; 17:1021-1024.*

"Japanese Application Serial No. 2009-549086, Office Action mailed Jan. 5, 2012", (w/ English Translation), 9 pgs.

"Australian Application Serial No. 2008216902, Request to Amend a Complete Specification and First Statement of Proposed Amendments filed Mar. 31, 2011", 10 pgs.

"Japanese Application Serial No. 2009-549086, Response filed May 7, 2012 to Office Action mailed Jan. 5, 2012", (w/ English Translation of Amended Claims), 11 pgs.

"International Application No. PCT/US2008/001467, Written Opinion mailed May 20, 2008", 6 pgs.

"International Application No. PCT/US2008/001467, International Search Report mailed May 20, 2008", 4 pgs.

Hundley, W. G., et al., "Cardiac Cycle-Dependent Changes in Aortic Area and Distensibility are Reduced in Older Patients Wirth Isolated Diastolic Heart Failure and Correlate With Exercise Intolerance", *Journal of the American College of Cardiology*, 38(3), (2001), 796-802.

Kawaguchi, M., et al., "Combined Ventricular Systolic and Arterial Stiffening in Patients With Heart Failure and Preserved Ejection Fraction", *Circulation*, 107(5), (2003), 714-720.

"European Application Serial No. 08725142.7, Communication mailed Jun. 8, 2010", 5 pgs.

"Japanese Application Serial No. 2009-549086, Office Action mailed Jun. 26, 2012", (w/ English Translation), 9 pgs.

"Australian Application Serial No. 2008216902, First Examiner Report mailed Aug. 3, 2010", 2 pgs.

"International Application Serial No. PCT/US2008/001467, International Preliminary Report on Patentability mailed Aug. 27, 2009", 8 pgs.

"Japanese Application Serial No. 2009-549086, Response mailed Sep. 14, 2012 to Office Action mailed Jun. 26, 2012", (w/ English Translation of Amended Claims), 8 pgs.

"European Patent Application No. 08725142.7, Response filed Oct. 13, 2010 to Office Action dated Jun. 8, 2010", 6 pgs.

* cited by examiner 70V, 0.5 ms, 1 Hz, CONTINUOUS 70V, 0.5 ms, 16 Hz, CONTINUOUS STIMULATION 70V, 0.5 ms, 16 Hz, 10s BURST 24Hz, 70V, 0.5 ms PULSES, 10 SEC ON/OFF

SYSTEMS AND METHODS FOR ELECTRICAL STIMULATION OF BLOOD VESSELS

TECHNICAL FIELD

This disclosure relates generally to medical devices, and more particularly systems and methods for electrical stimulation of blood vessels.

BACKGROUND

A number of medical conditions can be linked to problems with blood vessels. Vasoconstriction and vasodilation can be used to control cardiac output and are useful for a number of therapies. Improved systems and methods for providing vasoconstriction and/or vasodilation therapy are needed.

SUMMARY

The above-mentioned problems and others not expressly discussed herein are addressed by the present subject matter and will be understood by reading and studying this specification.

Disclosed herein, among other things, is a method for applying electrical vasodilation therapy. According to an embodiment, the method includes electrically stimulating smooth muscle of a vessel to dilate the vessel, including stimulating the smooth muscle at a predetermined frequency and a predetermined voltage and a predetermined duty cycle to decrease tonus of the smooth muscle. The method also includes sensing a physiological parameter and adjusting the electrical stimulation to the vessel based on the sensed physiological parameter, according to various embodiments.

Disclosed herein, among other things, is a method for applying vascular massage therapy. According to an embodiment, the method includes applying a first electrical stimulation therapy to a blood vessel at a first predetermined frequency and a first predetermined voltage and a first predetermined duty cycle to produce vascular dilation. The method also includes applying a second electrical stimulation therapy to the blood vessel at a second predetermined frequency and a second predetermined voltage and a second predetermined duty cycle to produce vascular constriction, according to an embodiment. The method further includes controlling timing and duration of dilation and constriction to increase vessel compliance, according to various embodiments.

Disclosed herein, among other things, is a method for applying vascular therapy to regulate blood pressure. According to one embodiment, the method includes applying electrical stimulation to a blood vessel at a frequency of at least 16 Hz and a voltage level of at least 10 Volts to produce vascular constriction. The method embodiment also includes controlling timing and duration of constriction to regulate blood pressure. According to various embodiments, the method further includes sensing at least one physiological parameter and adjusting timing and duration of constriction based on the sensed parameter.

Disclosed herein, among other things, is a vascular therapy system. According to one embodiment, the system includes at least one electrode having electrical contact with a blood vessel. The system embodiment also includes a stimulation circuit electrically connected to the electrode, the circuit adapted to provide stimulation to the vessel. The system embodiment further includes a controller connected to the circuit, the controller adapted to select frequency and voltage parameters for the stimulation circuit to selectively affect vascular therapy, including constriction of the vessel and dilation of the vessel. According to various embodiments, the stimulation circuit and controller are contained within an implantable medical device (IMD).

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Various embodiments of the present subject matter are related to systems and methods for electrical stimulation of blood vessels. Electrical waveforms with programmable predetermined frequencies and voltages are used to selectively dilate or constrict vessels to treat a number of medical conditions. In various embodiments, physiological parameters are sensed and stimulation adjusted in a closed loop therapy system. Providing electrical stimulation to a blood vessel to constrict the vessel is referred to as vasoconstriction. Electrical stimulation to dilate a vessel is referred to as vasodilation.

The present subject matter refers to direct stimulation of smooth muscle to produce vasodilation and vasoconstriction. Muscle tonus is decreased in the case of vasodilation and increased in the case of vasoconstriction. This contrasts with stimulation of a baroreceptive neural target or pressoreceptor to affect vessel diameter, in which the stimulation affects the central nervous system.

The stimulation of smooth muscle requires relatively high voltage and frequency, but lower frequencies (around 1 Hz) are used for affecting vasodilation therapy. This approach bypasses normal physiological processes that control vasoconstriction and vasodilation, so it can be applied in pathological situations, such as systolic and diastolic heart failure or hypertension, where normal control mechanisms (e.g. neural or biochemical/hormonal control) no longer function properly. Potential applications of this vasoconstriction or vasodilation therapy include, but are not limited to: stimulation of coronary arteries to prevent or counteract vasospasm during unstable angina; stimulation of an aorta to reduce afterload on the heart in hypertension or diastolic heart failure, particularly during exercise to reduce increases in systolic blood pressure; treating peripheral arteriosclerosis; ischemic pre-conditioning applications such as spinal cord protection; controlling kidney perfusion; and treatment of vascular aneurysms.

Figure 1:
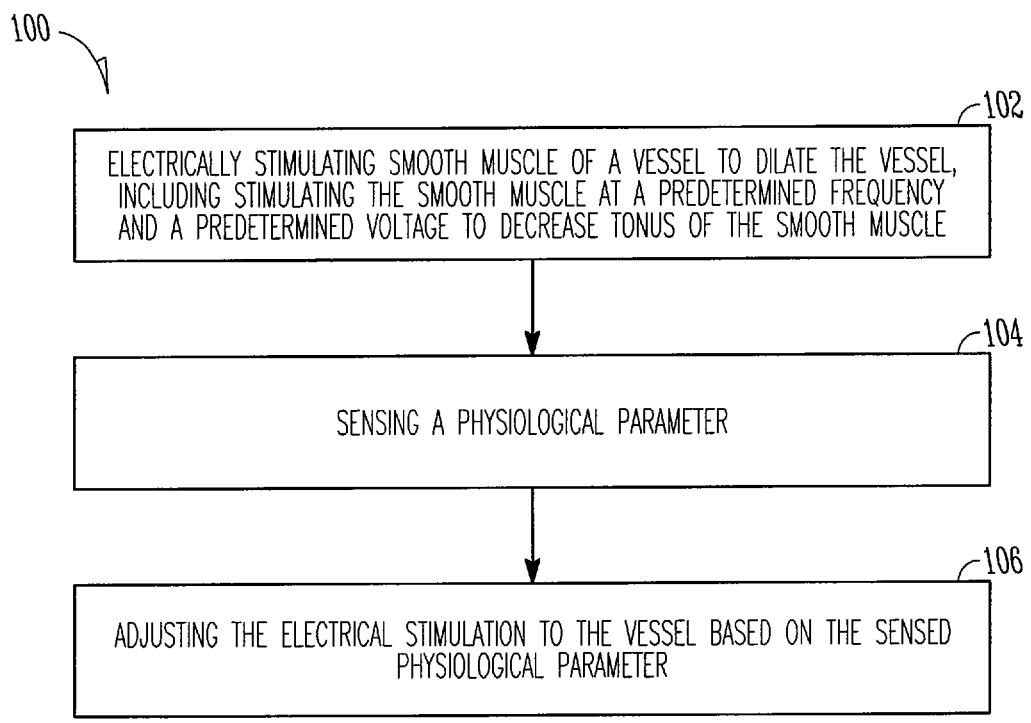
FIG. 1 illustrates a flow diagram of a method for applying electrical vasodilation therapy, according to one embodiment.

FIG. 1 illustrates a flow diagram of a method for applying electrical vasodilation therapy, according to one embodiment. The method 100 includes electrically stimulating smooth muscle of a vessel to dilate the vessel, including stimulating the smooth muscle at a predetermined frequency and a predetermined voltage to decrease tonus of the smooth muscle, at 102. The method also includes sensing a physiological parameter, at 104, and adjusting the electrical stimulation to the vessel based on the sensed physiological parameter, at 106.

According to various embodiments, the smooth muscle is stimulated at a predetermined duty cycle. Duty cycle refers to the relative length of time the pulsed stimulation is on and off, for example, continuous stimulation or a pattern of ten seconds on and ten seconds off, etc. According to various embodiments, applying electrical stimulation to dilate the vessel includes applying stimulation at a frequency of about 1 Hz. Applying electrical stimulation includes applying stimulation at a voltage of about 70 Volts, in an embodiment. Other voltages and frequencies may be used without departing from the scope of this disclosure.

Figure 5:
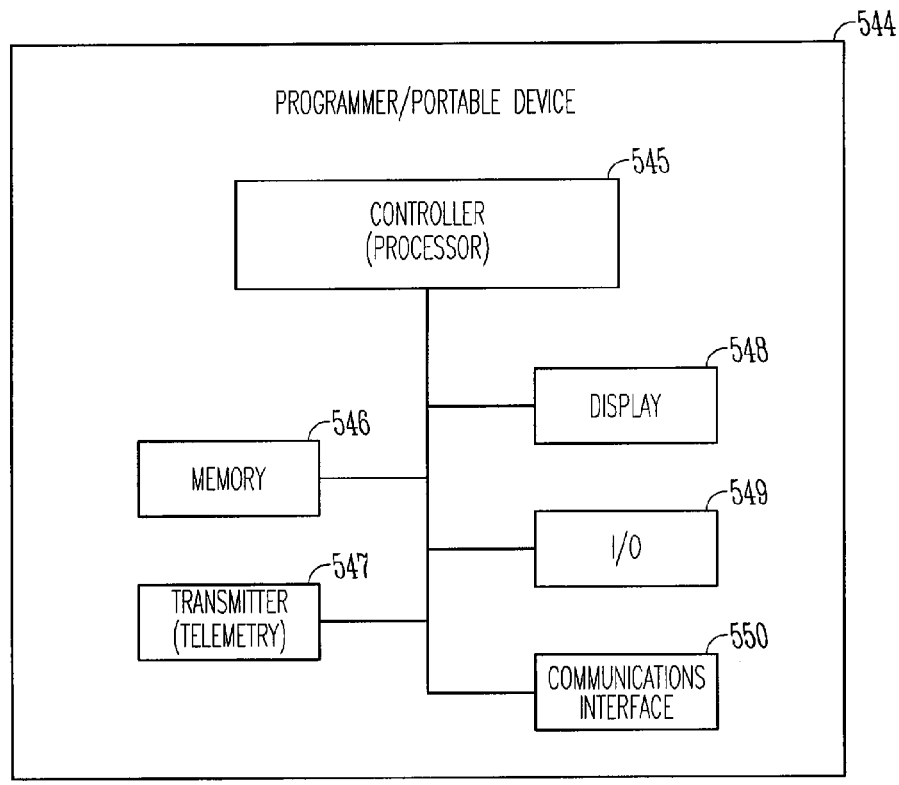
FIG. 5 illustrates a block diagram of a programmer such as illustrated in the system of FIG. 4 or other external device to communicate with the IMD(s), according to one embodiment.

According to varying embodiments, electrical stimulation can be applied using an external device, or using an implantable medical device (IMD). Types of IMDs include a stand-alone angina therapy device, a stand-alone hypertension therapy device, or a cardiac device such as a pulse generator. According to various embodiments, pulse generators include devices that function as various cardiac rhythm management (CRM) devices such as pacemakers, cardioverters/defibrillators, cardiac resynchronization therapy (CRT) devices, as well as combination devices that provide more than one of these therapy modalities to a subject. The pulse generator is programmably controlled by an external device via wireless communication, according to various embodiments. Examples of types of wireless communication used include, but are not limited to, radio frequency (RF) links and inductive telemetry. The pulse generator is powered by an internal or external battery, or a combination of internal and external batteries, in varying embodiments. In one embodiment, the pulse generator is adapted to be charged by the external battery prior to use. Examples of external devices include, but are not limited to, programmers (such as depicted in FIG. 5) and remote patient monitoring systems. The electrical stimulation function could also be incorporated into external systems for non-invasive applications, such as to increase local perfusion to improve wound healing, for example.

Figure 2:
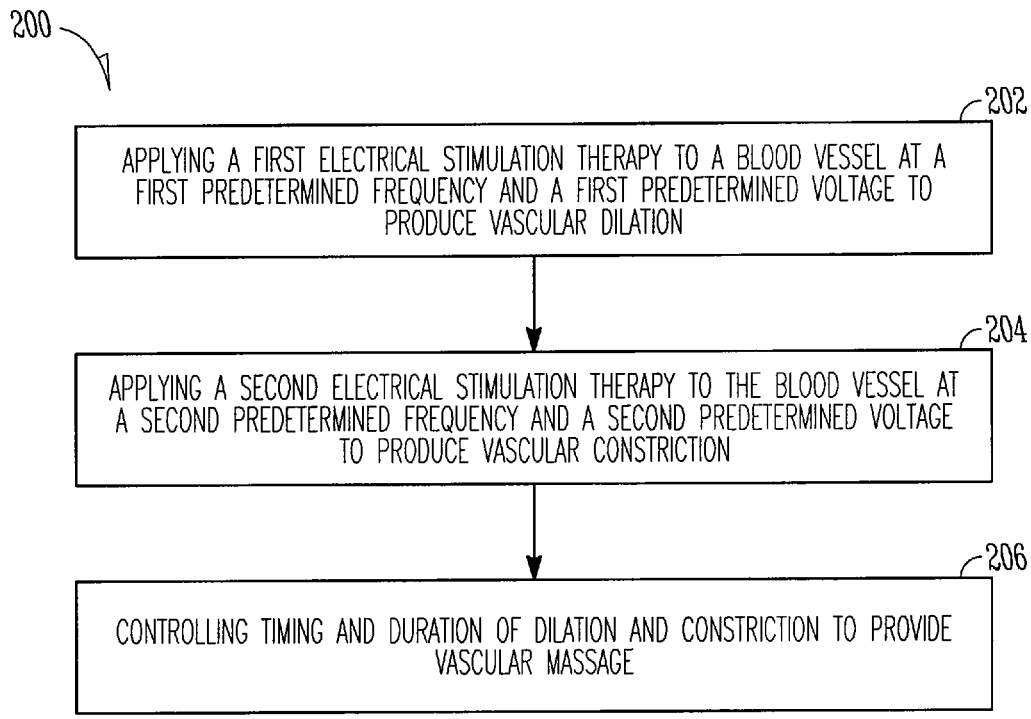
FIG. 2 illustrates a flow diagram of a method for applying vascular massage therapy, according to one embodiment.

FIG. 2 illustrates a flow diagram of a method for applying vascular massage therapy, according to one embodiment. The method 200 includes applying a first electrical stimulation therapy to a blood vessel at a first predetermined frequency and a first predetermined voltage to produce vascular dilation, at 202. The method also includes applying a second electrical stimulation therapy to the blood vessel at a second predetermined frequency and a second predetermined voltage to produce vascular constriction, at 204. The method further includes controlling timing and duration of dilation and constriction to increase vessel compliance, at 206. According to various embodiments, the smooth muscle is stimulated at a first predetermined duty cycle for vascular dilation and at a second predetermined duty cycle for vascular constriction.

Controlling timing and duration of dilation and constriction includes adjusting the vascular massage to increase vessel compliance, according to various embodiments. Applying the first electrical stimulation therapy to a blood vessel includes applying electrical stimulation to a descending aorta, in an embodiment, but can be applied to any artery or vessel without departing from the scope of the disclosure. Various embodiments of the method also include sensing at least one physiological parameter and adjusting timing and duration of dilation and constriction based on the sensed parameter. Examples of sensed physiological parameters for a closed loop system include, but are not limited to, blood pressure and blood vessel diameter. In various embodiments, timing and duration are programmably controlled. Stimulation is provided intermittently, periodically, or according to a predetermined schedule, in varying embodiments. According to various embodiments, vascular massage includes applying vasodilation at approximately 1 Hz, up to 70 Volts, for several minutes. Vascular massage includes applying vasoconstriction at 10 or more Volts and 16 or more Hz, according to various embodiments. Voltage levels of approximately 70 Volts provide the greatest amount of vessel contraction. Aortic blood pressure is decreased when stimulating at this level. In one embodiment, vasoconstriction is applied from 10 or more seconds, then stopped for 10 or more seconds (duty cycle), then repeated, to provide vascular massage. A pulse width of approximately 0.5 msec is used for vasoconstriction, in an embodiment. Vasoconstriction and vasodilation are applied alternately with a period of 10's of seconds to minutes to provide vascular massage, according to varying embodiments.

The vascular massage therapy can be provided continuously or at certain times during the day, such as for one half hour per day in an embodiment. The times of therapy can be programmable at certain intervals, or based on physiologic response to measurable parameters such as heart rate variability, activity monitors, or other parameters. According to varying embodiments, the therapy is titrated remotely, for example using a programmer (such as the programmer in FIG. 5) coupled to a Sphygmacor or Omron's augmentation index) analyzer. Other forms of energy such as thermal, microwave or ultrasound may be used to provide similar therapy. Vascular massage therapy can be used in any device discussed with respect to vasodilation therapy above, and can also be incorporated into stent based pacing systems to provide massage for occluded/infarct related arteries.

Figure 10:
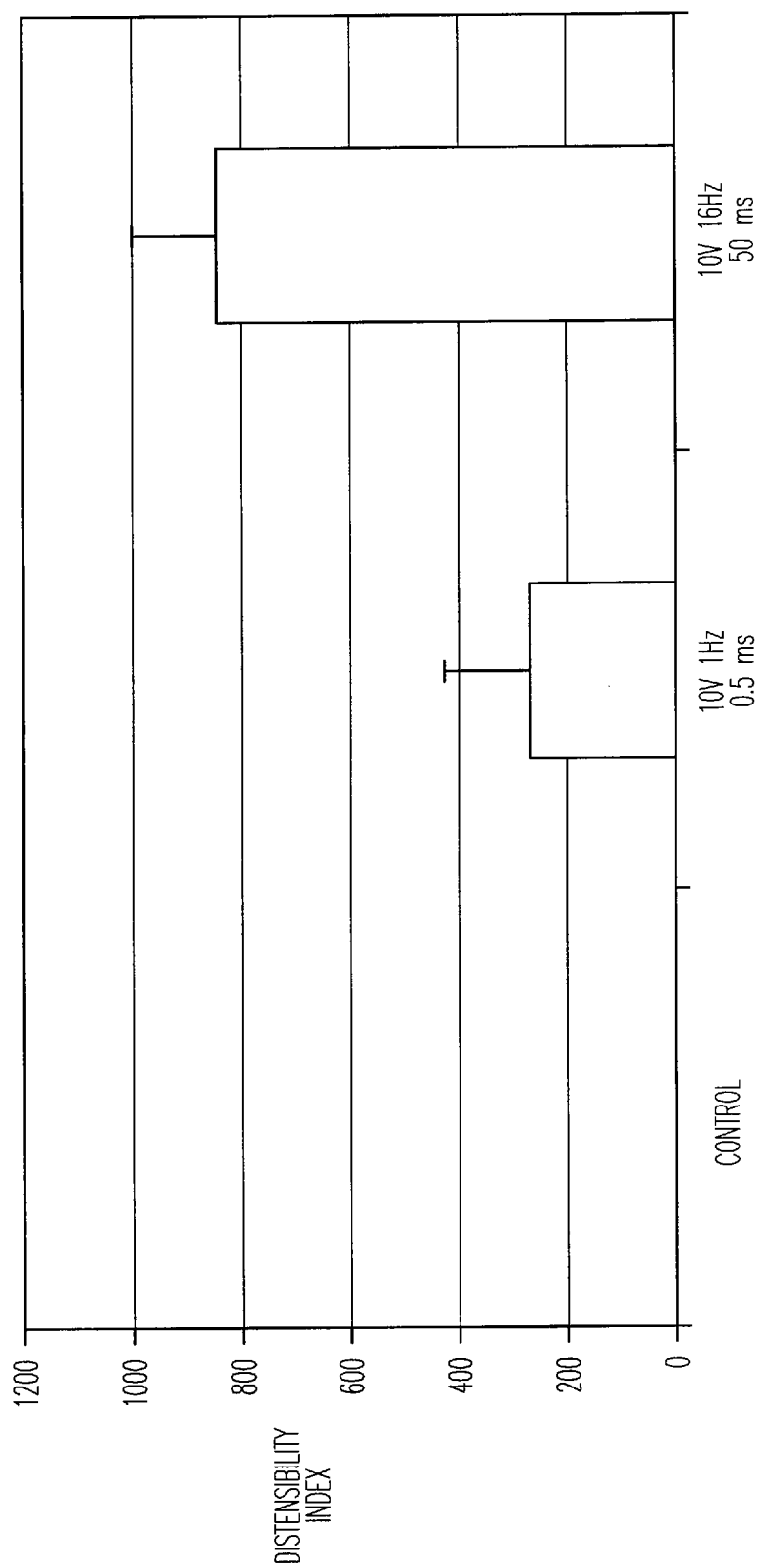
FIG. 10 illustrates a graphical diagram of applied electrical stimulation therapy, according to various embodiments.

Advanced patient age or disease can result in increasing stiffness of vasculature, which is associated with hypertension and diastolic heart failure. The ability to control vasodilation and vasoconstriction through electrical stimulation is useful in producing vascular massage, which can be used to increase vessel compliance. Vessel compliance refers to the unit change in vessel cross-sectional area per unit change in applied pressure, and is a measure of the elasticity of the vessel. Increasing vessel compliance has implications in several pathological conditions, including hypertension, systolic and diastolic heart failure, and vascular diseases. In addition, peripheral resistance of the vessel ($E_a$) is decreased thereby improving impedance matching and pump efficiency. $E_a$ is defined as the ratio of the change in pressure to the change in volume during a cardiac ejection, and is normally computed by dividing the end-systolic pressure by the stroke volume. In addition, the application of electrical stimulation increases the distensibility of the aorta locally. This can have the effect of reducing a reflected pressure wave in the aorta, which is beneficial in preventing further structural damage. The distensibility index (DI) can be calculated using the following equation:

$$DI=(dA/A)/dP\times 1000$$

Where A is the diastolic luminal area, dA is the difference between the smallest and largest luminal areas, and dP is the pulse pressure. An increase in aortic DI is also beneficial in propelling blood forward through systemic circulation. In addition, the coupling between the ventricle and the coronary vasculature can be improved with the increase in aortic DI. FIG. 10 illustrates a graphical diagram of applied electrical stimulation therapy, according to various embodiments. Electrical stimulation is shown to increase distensibility relative to a control condition using a stimulation waveform of 10 Volts, at 1 and 16 Hz, and 0.5 and 50 msec pulse widths. Other electrical stimulation waveforms can be used to increase distensibility without departing from the scope of this disclosure.

Figure 3:
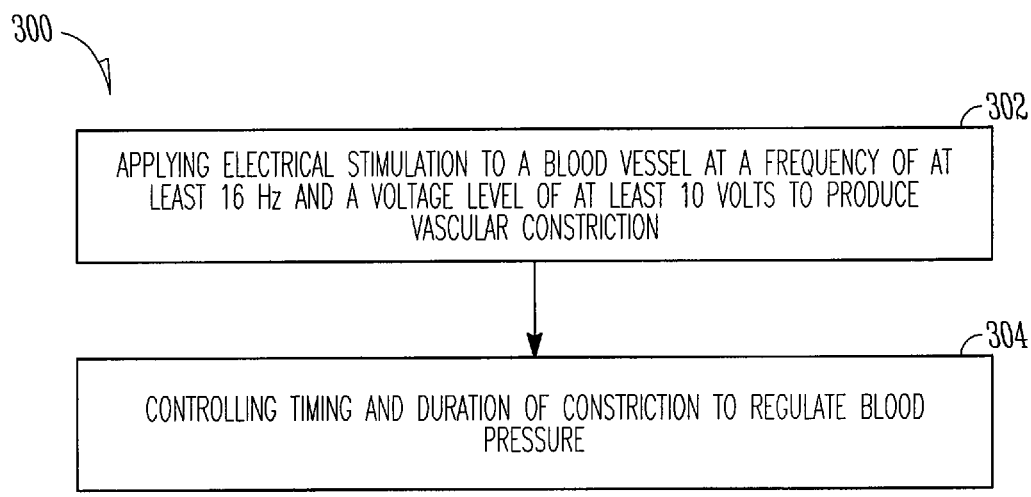
FIG. 3 illustrates a flow diagram of a method for applying vascular therapy to regulate blood pressure, according to one embodiment.

FIG. 3 illustrates a flow diagram of a method for applying vascular therapy to regulate blood pressure, according to one embodiment. The method 300 includes applying electrical stimulation to a blood vessel at a frequency of at least 16 Hz and a voltage level of at least 10 Volts to produce vascular constriction, at 302. The method embodiment also includes controlling timing and duration of constriction to regulate blood pressure, at 304. The vasoconstriction method is not limited to blood pressure regulation, and can also be used for other therapies, including but not limited to: stimulation of coronary arteries to prevent or counteract vasospasm during unstable angina; stimulation of an aorta to reduce afterload on the heart in hypertension or diastolic heart failure, particularly during exercise to reduce increases in systolic blood pressure; treating peripheral arteriosclerosis; ischemic preconditioning applications such as spinal cord protection; controlling kidney perfusion; and treatment of vascular aneurysms. According to various embodiments, the method further includes sensing at least one physiological parameter and adjusting timing and duration of constriction based on the sensed parameter.

Applying electrical stimulation includes applying stimulation at a voltage level of at least 70 Volts at a frequency of about 16 Hz for a duration of approximately 10 seconds, according to an embodiment. In one embodiment, electrical stimulation is applied to the descending aorta to regulate systemic blood pressure. Blood pressure is sensed and electrical stimulation applied when the sensed blood pressure increases above a first threshold and is ceased when sensed blood pressure decreases below a second threshold, in various embodiments. The first and second thresholds are programmable parameters in one embodiment. A system for blood pressure regulation includes a stand-alone system (either external or internal), according to an embodiment. In another embodiment, the system for blood pressure regulation is incorporated into an existing IMD (as in FIG. 4) having electrodes for stimulating vessels and sensors for monitoring blood pressure.

Potential applications of this technology include, but are not limited to, intelligent blood pressure regulation when coupled with an internal blood pressure sensor, intermittent blood pressure reduction during acute blood pressure crisis, regulation of blood flow such as creating transient ischemia, reducing hemorrhage or preventing bleeding during surgery, and therapy for reducing the size of vascular aneurysms. This vascular therapy would also be beneficial for treating diastolic heart failure by regulating resting blood pressure and decreasing major spikes in blood pressure which occur during exercise.

Figure 4:
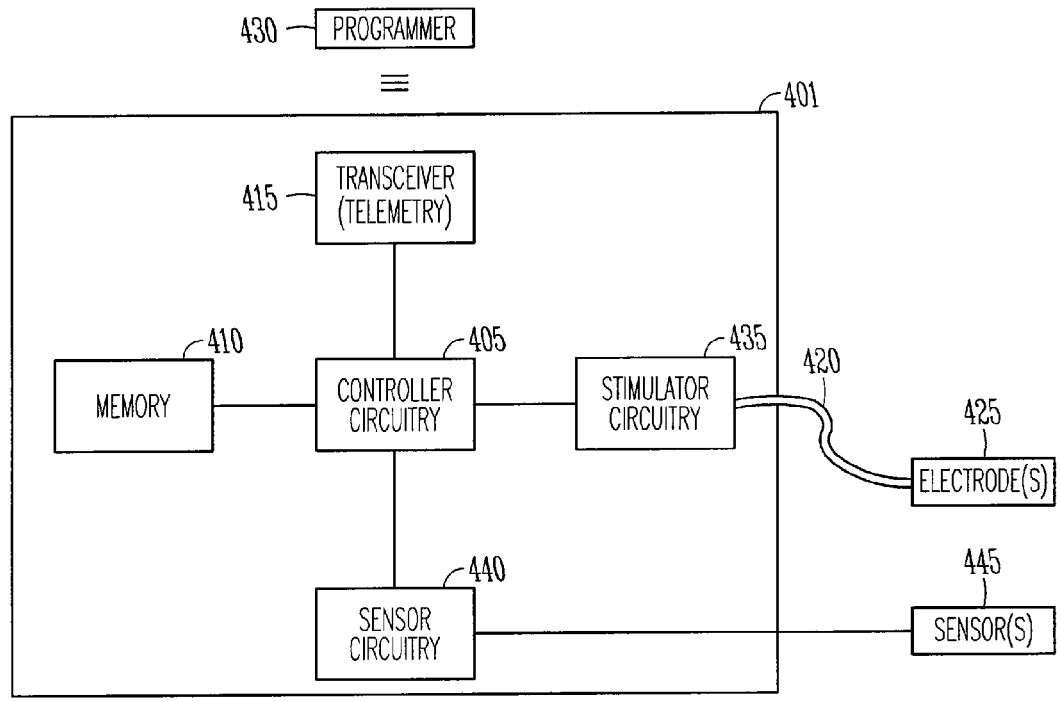
FIG. 4 illustrates a block diagram of a system with an implantable medical device (IMD), according to one embodiment.

FIG. 4 illustrates a block diagram of a system with an implantable medical device (IMD), according to one embodiment. The system includes an IMD 401, an electrical lead 420 coupled to the IMD 401, and at least one electrode 425. The IMD includes a controller circuit 405, a memory circuit 410, a telemetry circuit 415, and a stimulation circuit 435. The controller circuit 405 is operable on instructions stored in the memory circuit to deliver an electrical stimulation therapy. Therapy is delivered by the stimulation circuit 435 through the lead 420 and the electrode(s) 425. The telemetry circuit 415 allows communication with an external programmer 430. The programmer 430 is used to adjust the programmed therapy provided by the IMD 401, and the IMD reports device data (such as battery capacity and lead resistance) and therapy data (such as sense and stimulation data) to the programmer using radio telemetry, for example. The illustrated system also includes sensor circuitry 440 that is connected to at least one sensor 445. According to various embodiments, the sensor 445 is adapted to sense a physiological parameter and the controller 405 adjusts the electrical stimulation to the vessel based on the sensed physiological parameter, using the method of FIG. 1, for example. According to various embodiments, the disclosed systems and methods are used with a leadless device. For example, in an embodiment, one or more satellite electrodes are controlled wirelessly to deliver electrical therapy. In addition, the lead can be configured to include both sensors and electrodes, or combination elements capable of sensing and stimulating.

FIG. 5 illustrates a block diagram of a programmer 544, such as the programmer 430 illustrated in the system of FIG. 4 or other external device to communicate with the IMD(s), according to one embodiment. Examples of other external devices include Personal Digital Assistants (PDAs), personal laptop and desktop computers in a remote patient monitoring system, or a handheld device in such a system. The illustrated device 544 includes controller circuitry 545 and a memory 546. The controller circuitry 545 is capable of being implemented using hardware, software, and combinations of hardware and software. For example, according to various embodiments, the controller circuitry 545 includes a processor to perform instructions embedded in the memory 546 to perform a number of functions, including communicating data and/or programming instructions to the devices. The illustrated device 544 further includes a transceiver 547 and associated circuitry for use to communicate with a device. Various embodiments have wireless communication capabilities. For example, various embodiments of the transceiver 547 and associated circuitry include a telemetry coil for use to wirelessly communicate with a device. The illustrated device 544 further includes a display 548, input/output (I/O) devices 549 such as a keyboard or mouse/pointer, and a communications interface 550 for use to communicate with other devices, such as over a communication network.

Figure 6:
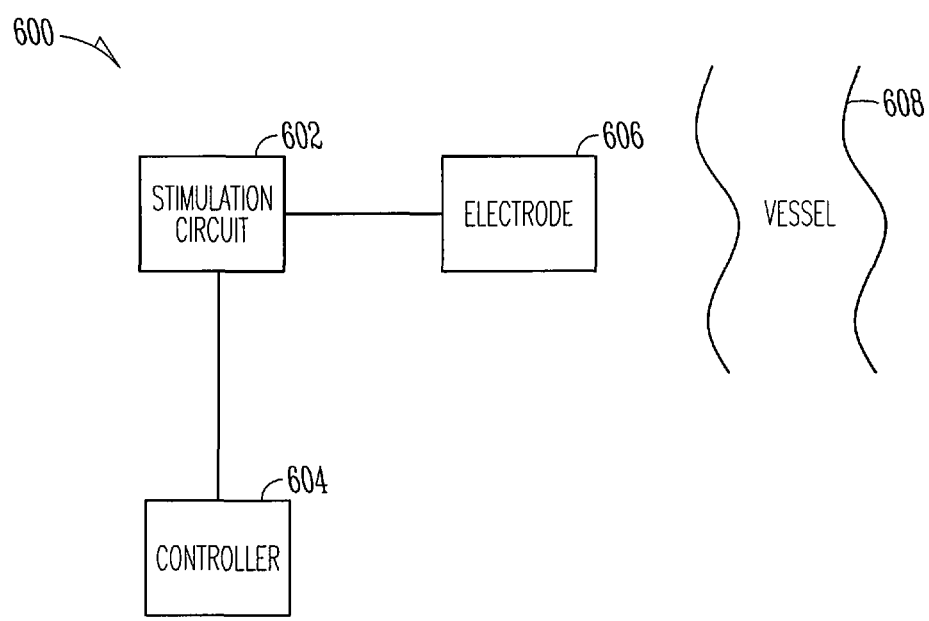
FIG. 6 illustrates a block diagram of a vascular therapy system, according to one embodiment.

FIG. 6 illustrates a block diagram of a vascular therapy system, according to one embodiment. The system 600 includes at least one electrode 606 having electrical contact with a blood vessel 608. The system embodiment also includes a stimulation circuit 602 electrically connected to the electrode, the circuit adapted to provide stimulation to the vessel. The system embodiment further includes a controller 604 connected to the circuit, the controller adapted to select frequency and voltage parameters for the stimulation circuit to selectively affect vascular therapy, including constriction of the vessel and dilation of the vessel. According to various embodiments, the stimulation circuit and controller are contained within an implantable medical device (IMD). As discussed, the IMD may include a stand-alone dedicated vascular stimulation device, or a combination device including functions such as defibrillation, CRT, or pacing, for example. The electrode need not be in physical contact with the vessel to provide stimulation, according to varying embodiments, but if no direct contact exists, voltage requirements for the therapy increase. In one embodiment, vascular stimulation is affected percutaneously.

According to various embodiments, the electrode is wirelessly connected to the stimulation circuit. A lead is connected between the electrode and the stimulation circuit, in varying embodiments. Examples of leads used include, but are not limited to, standard pacing leads or intravascular stent pacing leads. A sensor is connected to the controller, and the controller initiates or alters therapy based on a signal received from the sensor, in various embodiments. Types of sensors used include, but are not limited to, an internal sensor such as a vascular diameter sensor (using ultrasonic crystals, for example), a minute ventilation sensor, an accelerometer, a heart rate sensor, an impedance or blood volume sensor, a blood flow sensor (using an ultrasonic probe, for example), or a chronic pressure sensor, and/or an external sensor such as an augmentation index analyzer, or a blood pressure cuff. More than one sensor and more than one electrode can be used without departing from the scope of this disclosure. According to various embodiments, the controller (when the controller is in an IMD) initiates or alters therapy based on a signal received from an external source via wireless telemetry. In varying embodiments radio frequency telemetry, inductive telemetry, or other types of wireless communication may be used to transmit and receive signals to one or more external sources.

The system of FIG. 6, or similar IMD of FIG. 4, can be utilized for immediate vasoconstrictive effect, longer vasodilation effect, or a periodic effect. Multiple leads and electrodes can be used with single or multiple vascular sites, or sequential pacing of upstream or downstream sites. In addition, leadless pacing is utilized in this system in various embodiments.

Figure 7A:
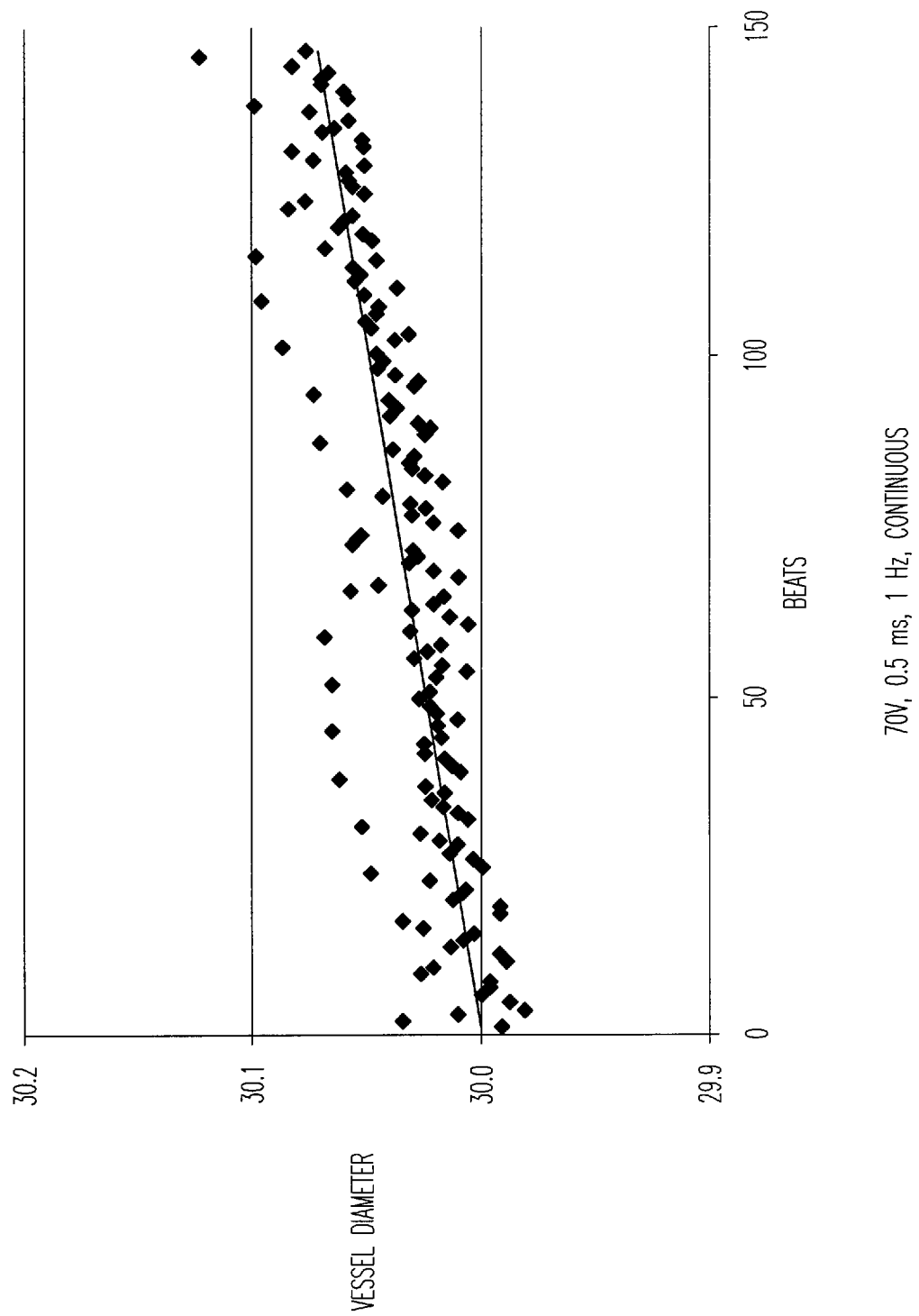
FIGS. 7A-7B illustrate graphical diagrams of applied vasodilation and vasoconstriction therapy, according to various embodiments.
Figure 7B:
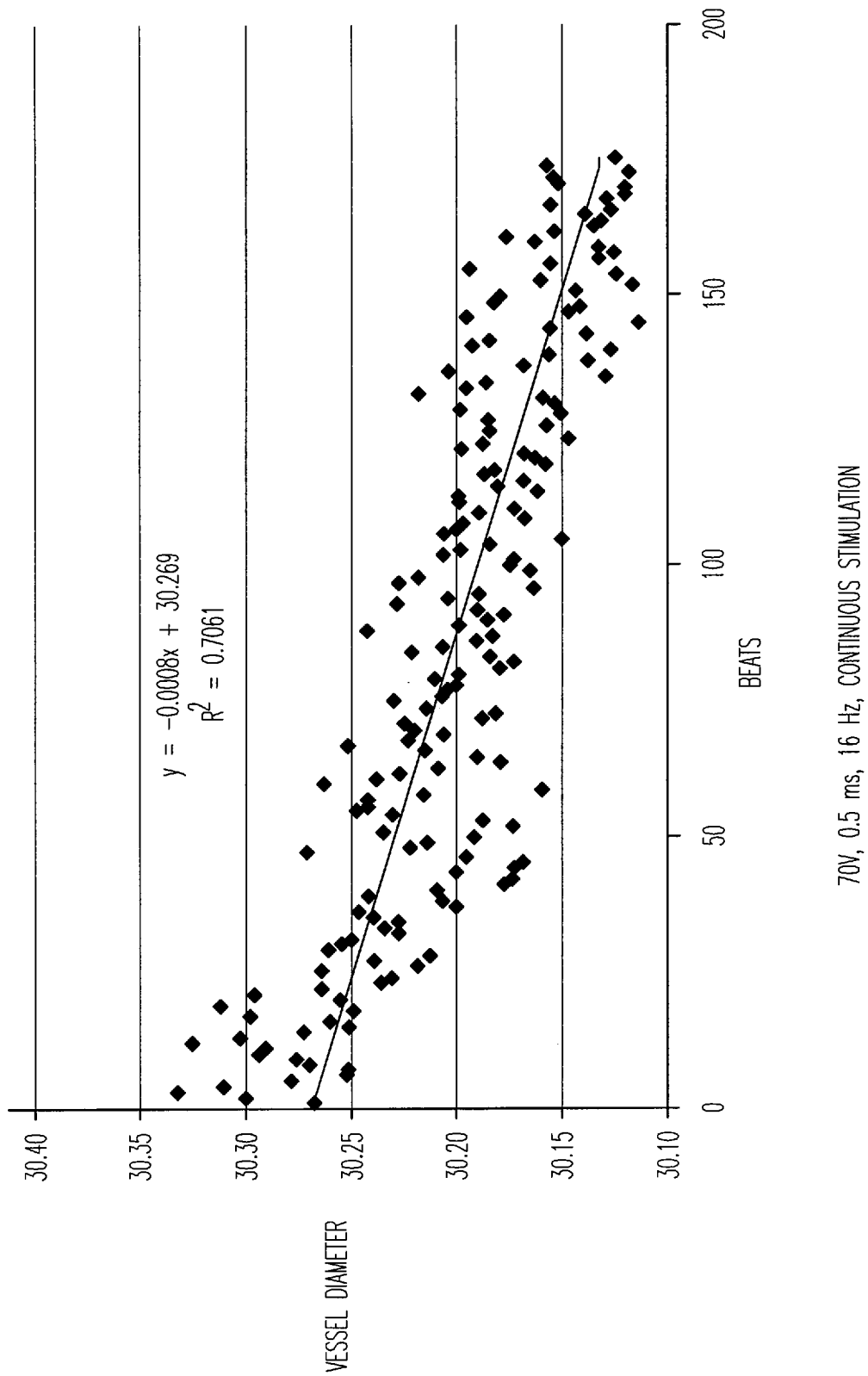

FIGS. 7A-7B illustrate graphical diagrams of applied vasodilation and vasoconstriction therapy, according to various embodiments. FIG. 7A illustrates a graphical diagram of resulting vessel dilation (vessel diameter in millimeters) using an electrical waveform produced at or near a blood vessel, using the method of FIG. 1, for example. The waveform has an amplitude of 70 Volts and is applied continuously at 1 Hz with a pulse-width of 0.5 msec. FIG. 7B illustrates a graphical diagram of resulting vessel constriction (in millimeters) using an electrical waveform produced at or near a blood vessel. The waveform has an amplitude of 70 Volts and is applied continuously at 16 Hz with a pulse-width of 0.5 msec. These waveforms are examples, and other waveforms can be used, as discussed above, without departing from the scope of this disclosure.

Figure 8A:
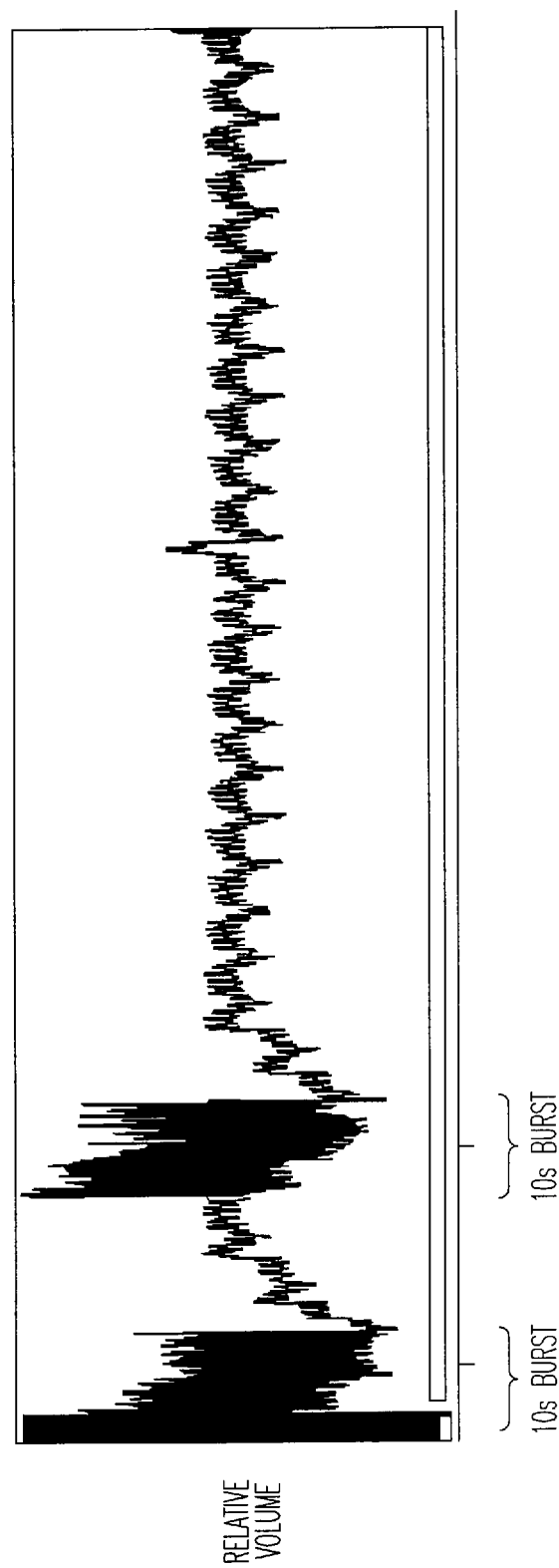
FIGS. 8A-8B illustrate graphical diagrams of applied vascular massage therapy, according to various embodiments.
Figure 8B:
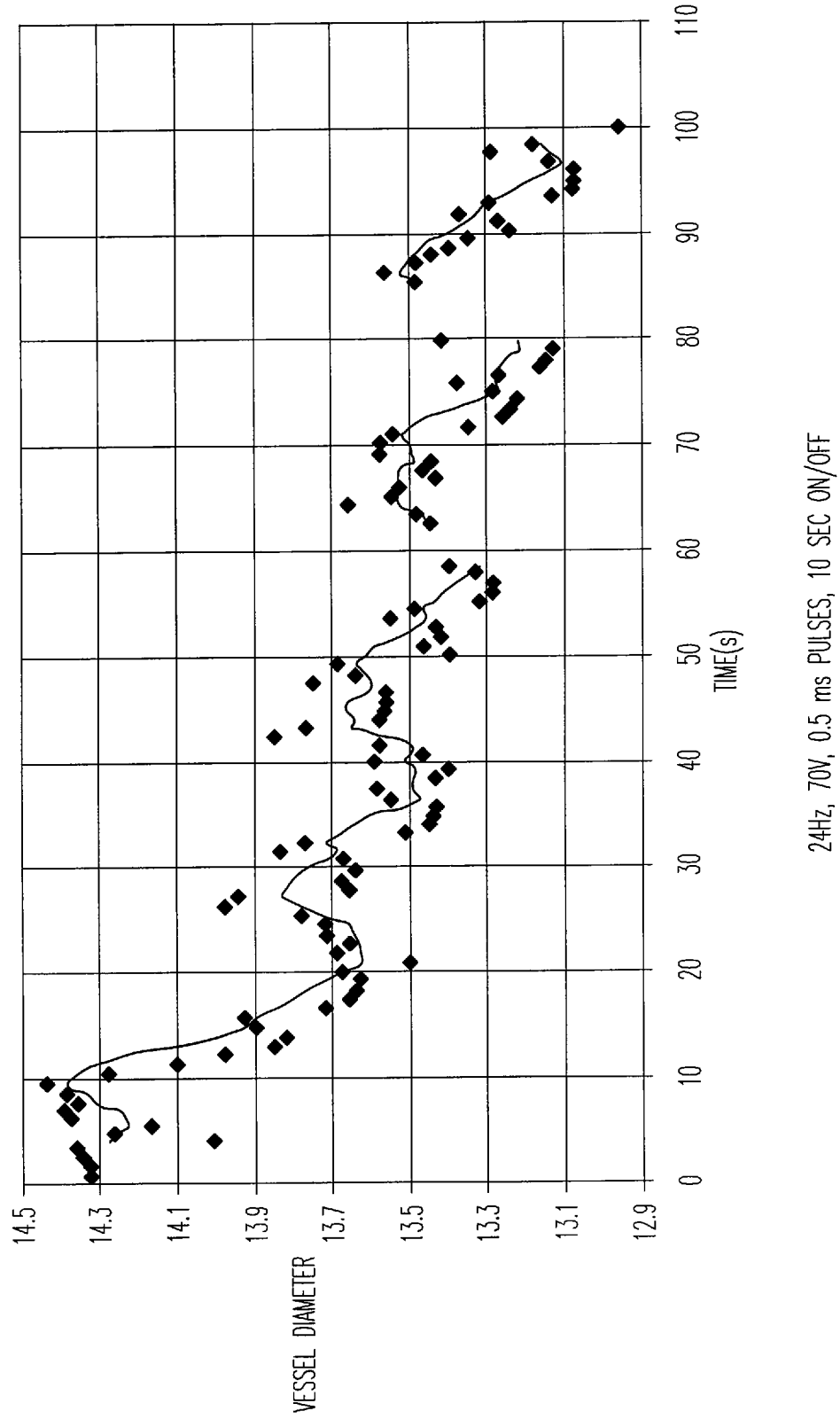

FIGS. 8A-8B illustrate graphical diagrams of applied vascular massage therapy, according to various embodiments. FIG. 8A illustrates a graphical diagram of resulting vessel volume using electrical waveforms produced at or near a blood vessel, using the method of FIG. 2, for example. The waveform has an amplitude of 70 Volts and is applied in 10 second bursts at 16 Hz with a pulse-width of 0.5 msec to massage the vessel. FIG. 8B illustrates a graphical diagram of resulting vessel constriction (in millimeters) using an electrical waveform produced at or near a blood vessel, using the method of FIG. 2, for example. The waveform has an amplitude of 70 Volts and is applied in 10 second bursts (10 seconds on, 10 seconds off) at 24 Hz with a pulse-width of 0.5 msec to massage the vessel. These waveforms are examples, and other waveforms can be used, as discussed above, without departing from the scope of this disclosure.

Figure 9A:
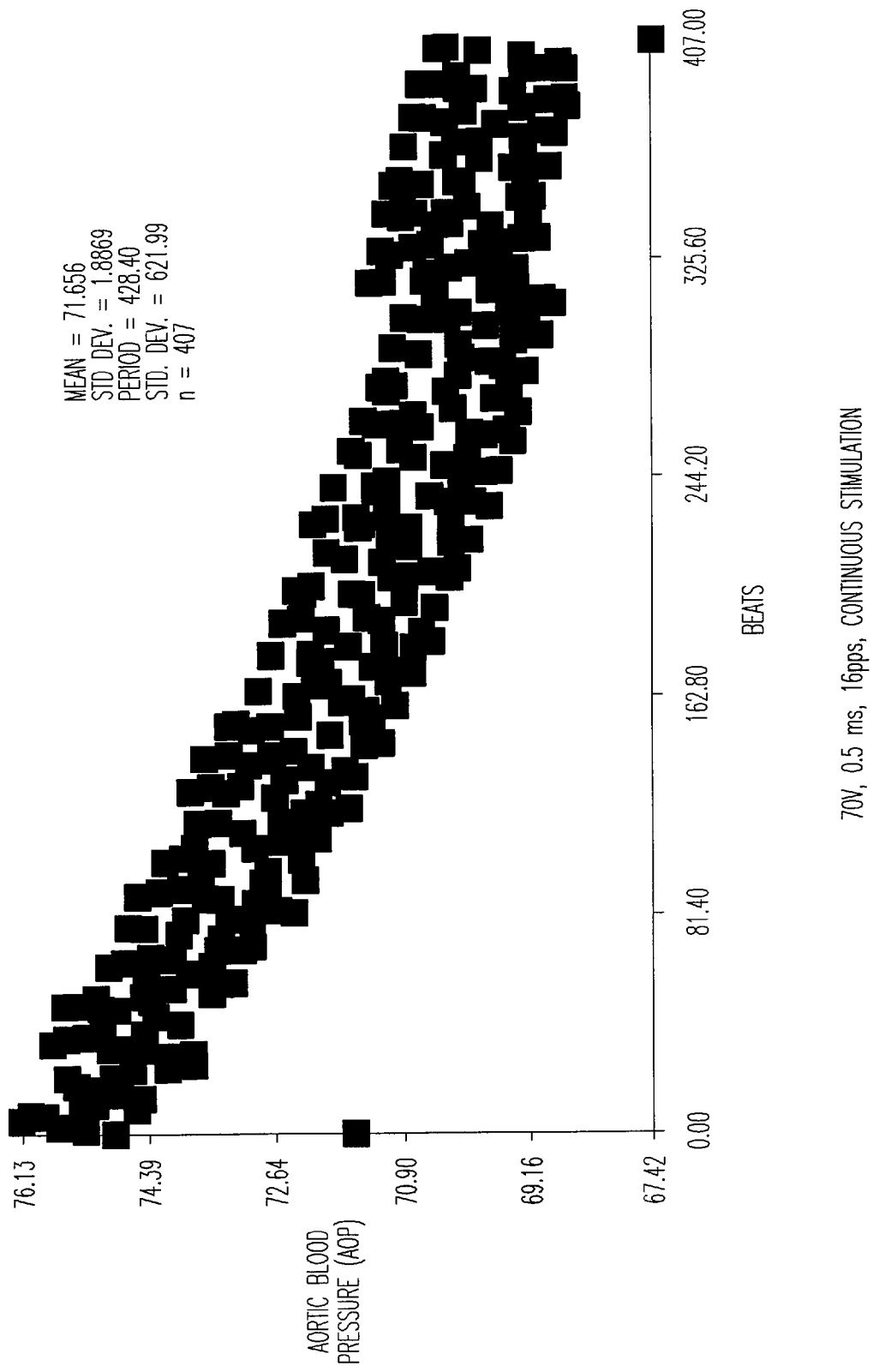
FIGS. 9A-9B illustrate graphical diagrams of applied blood pressure regulation therapy, according to various embodiments.
Figure 9B:
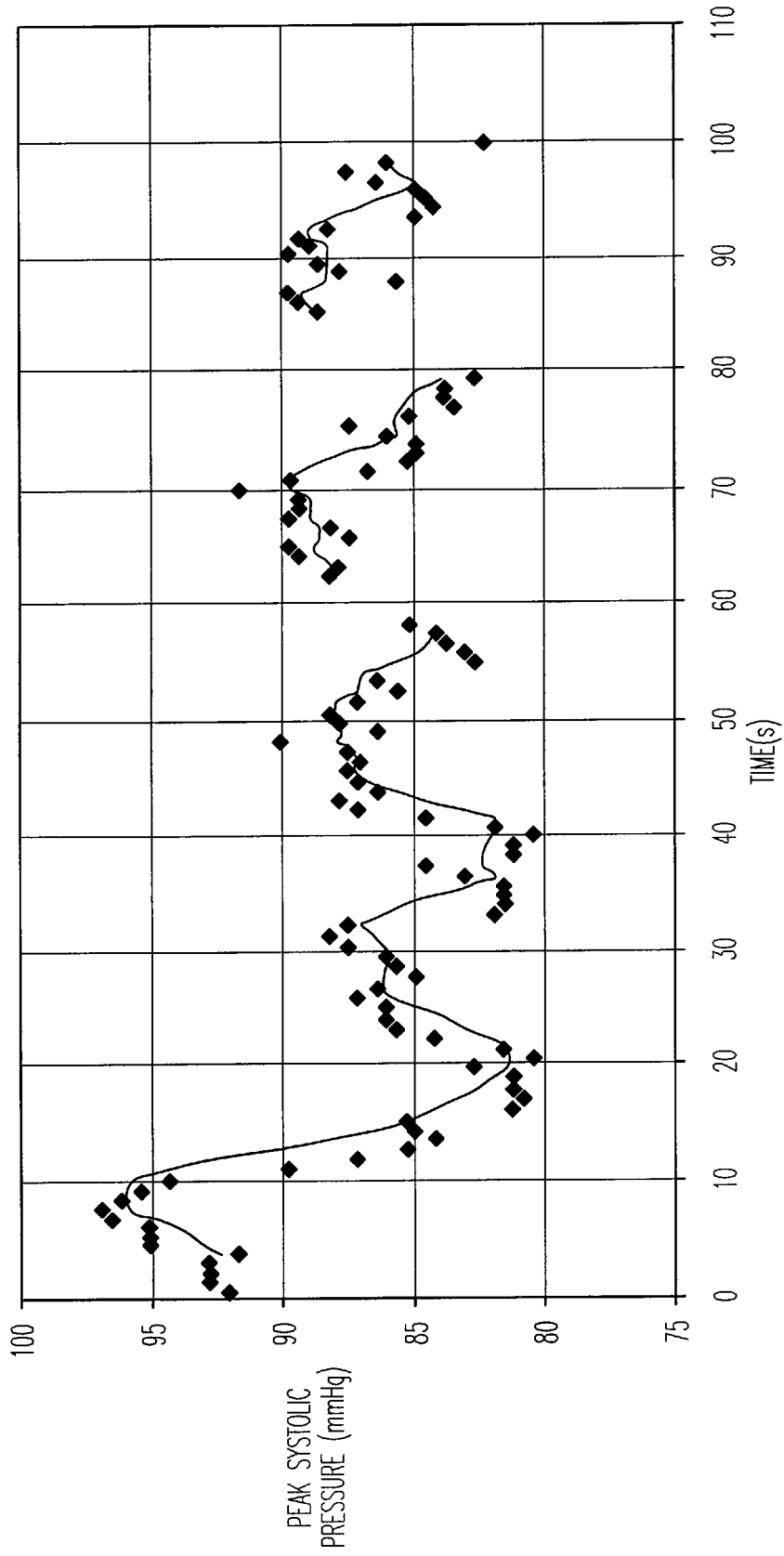

FIGS. 9A-9B illustrate graphical diagrams of applied blood pressure regulation therapy, according to various embodiments. FIG. 9A illustrates a graphical diagram of resulting diastolic blood pressure using an electrical waveform produced at or near a descending aorta, using the method of FIG. 3, for example. Other blood vessels (a renal artery for example) can be similarly stimulated to affect localized blood pressure reduction. The waveform has an amplitude of 70 Volts and is applied continuously at 16 Hz with a pulse-width of 0.5 msec. FIG. 9B illustrates a graphical diagram of peak systolic pressure using an electrical waveform produced at or near a vessel, using the method of FIG. 3, for example. The waveform has an amplitude of 70 Volts and is applied in 10 second bursts at 24 Hz with a pulse-width of 0.5 msec.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments, and other embodiments will be apparent to those of skill in the art upon reviewing the above description. The scope of the present subject matter should be determined with reference to the appended claims, along with the full scope of equivalents to which such claims are entitled.

We claim:

1. A method for electrically massaging a blood vessel, comprising:
   dilating the vessel, wherein dilating the vessel includes electrically stimulating smooth muscle of the vessel at a predetermined frequency and a predetermined voltage and a predetermined duty cycle to decrease tonus of the smooth muscle;
   constricting the vessel, wherein constricting the vessel includes electrically stimulating smooth muscle of the vessel at a predetermined frequency and a predetermined voltage and a predetermined duty cycle to increase tonus of the smooth muscle;

providing vascular massage, wherein providing vascular massage includes alternating electrical stimulation for vessel dilation and vessel constriction;
sensing a physiological parameter; and
adjusting the electrical stimulation to the vessel based on the sensed physiological parameter.

2. The method of claim 1, wherein dilating the vessel includes electrically stimulating smooth muscle at a frequency of about 1 Hz.

3. The method of claim 1, wherein dilating the vessel includes electrically stimulating smooth muscle at a voltage of about 70 Volts.

4. The method of claim 1, wherein the predetermined duty cycle for dilating the vessel includes a continuous duty cycle.

5. The method of claim 1, wherein electrically stimulating smooth muscle includes applying stimulation using an implantable device.

6. The method of claim 5, wherein applying stimulation using an implantable device includes applying stimulation using a stand-alone angina therapy device.

7. The method of claim 5, wherein applying stimulation using an implantable device includes applying stimulation using a stand-alone hypertension therapy device.

8. The method of claim 5, wherein applying stimulation using an implantable device includes applying stimulation using a cardiac device.

9. A method for electrically massaging a blood vessel, comprising:
dilating the vessel, wherein dilating the vessel includes applying a first electrical stimulation therapy to the vessel at a first predetermined frequency and a first predetermined voltage and a first predetermined duty cycle;
constricting the vessel, wherein constricting the vessel includes applying a second electrical stimulation therapy to the vessel at a second predetermined frequency and a second predetermined voltage and a second predetermined duty cycle; and
providing vascular massage, wherein providing vascular massage includes alternating dilation and constriction and controlling timing and duration of dilation and constriction.

10. The method of claim 9, wherein controlling timing and duration of dilation and constriction includes adjusting the vascular massage to increase vessel compliance.

11. The method of claim 9, wherein applying the first electrical stimulation therapy to a blood vessel includes applying electrical stimulation to a descending aorta.

12. The method of claim 9, further comprising:
sensing at least one physiological parameter; and
adjusting timing and duration of dilation and constriction based on the sensed parameter.

13. The method of claim 12, wherein sensing a physiological parameter includes sensing blood pressure.

14. The method of claim 12, wherein sensing a physiological parameter includes sensing blood vessel diameter.

15. A method, comprising:
massaging a blood vessel, wherein massaging the blood vessel includes dilating and constricting the vessel,
wherein constricting the blood vessel includes:
applying electrical stimulation to a blood vessel at a frequency of at least 16 Hz and a voltage level of at least 10 Volts to produce vascular constriction; and
controlling timing and duration of constriction to regulate therapy.

16. The method of claim 15, wherein controlling timing and duration of constriction to regulate therapy includes controlling timing and duration of constriction to regulate blood pressure.

17. The method of claim 15, wherein applying electrical stimulation includes a voltage level of at least 70 Volts.

18. The method of claim 15, further comprising:
sensing at least one physiological parameter; and
adjusting timing and duration of constriction based on the sensed parameter.

19. The method of claim 18, wherein sensing a physiological parameter includes sensing blood pressure.

20. The method of claim 19, wherein electrical stimulation is applied when sensed blood pressure increases above a first threshold and is ceased when sensed blood pressure decreases below a second threshold.

21. The method of claim 20, wherein the first and second thresholds are programmable parameters.

22. A system for stimulating a blood vessel to affect vascular therapy, comprising:
at least one electrode adapted for electrical contact with the vessel;
a stimulation circuit electrically connected to the electrode, the circuit adapted to provide stimulation to the vessel; and
a controller connected to the circuit, the controller adapted to select frequency and voltage parameters for the stimulation circuit to selectively affect vascular therapy, including alternating constriction of the vessel and dilation of the vessel to provide vascular massage.

23. The system of claim 22, further comprising an implantable medical device (IMD), and wherein the stimulation circuit and controller are contained within the IMD.

24. The system of claim 23, further comprising a sensor connected to the controller.

25. The system of claim 24, wherein the IMD initiates or alters therapy based on a signal received from the sensor.

26. The system of claim 23, wherein the IMD initiates or alters therapy based on a signal received from an external source via wireless telemetry.

* * * * *